US008367077B2

(12) United States Patent
Zurbriggen et al.

(10) Patent No.: US 8,367,077 B2
(45) Date of Patent: Feb. 5, 2013

(54) VIROSOMES COMPRISING HEMAGGLUTININ DERIVED FROM AN INFLUENZA VIRUS PRODUCED IN A CELL LINE, COMPOSITIONS, METHODS OF MANUFACTURING, USE THEREOF

(75) Inventors: Rinaldo Zurbriggen, Schmitten (CH); Christian Moser, Bern (CH); Andreas Kammer, Zollikofen (CH); Mario Amacker, Schmitten (CH); Nicole Westerfeld, Rubigen (CH); Silvia Rasi, Zürich (CH)

(73) Assignee: Pevion Biotech, AG, Ittlingen (CH)

( * ) Notice: Subject to any disclaimer, the term of this patent is extended or adjusted under 35 U.S.C. 154(b) by 41 days.

(21) Appl. No.: 12/666,260

(22) PCT Filed: Jun. 13, 2008

(86) PCT No.: PCT/EP2008/004780
§ 371 (c)(1),
(2), (4) Date: Sep. 16, 2010

(87) PCT Pub. No.: WO2009/000433
PCT Pub. Date: Dec. 31, 2008

(65) Prior Publication Data
US 2011/0045057 A1     Feb. 24, 2011

(30) Foreign Application Priority Data
Jun. 22, 2007   (EP) .................................... 07012283

(51) Int. Cl.
*A61K 47/00*       (2006.01)
*A61K 9/127*       (2006.01)
(52) U.S. Cl. ..................................... 424/278.1; 977/802
(58) Field of Classification Search ......................... None
See application file for complete search history.

(56) References Cited

U.S. PATENT DOCUMENTS 5,672,485 A   9/1997  Foster et al.
5,989,805 A   11/1999 Reilly et al.

FOREIGN PATENT DOCUMENTS

| EP | 0 538 437 B1 | 5/1992 |
| EP | 1 652 914 A1 | 5/2006 |
| EP | 1 797 895 A1 | 6/2007 |
| EP | 1 938 835 A1 | 7/2008 |
| WO | WO92/19267 | 11/1992 |
| WO | WO96/33738 | 10/1996 |
| WO | WO2004/071492 | 8/2004 |
| WO | WO2004/106366 | 12/2004 |
| WO | WO2005/107797 | 11/2005 |
| WO | WO2006/108846 | 10/2006 |
| WO | WO2007/052058 | 5/2007 |
| WO | WO2007/052059 | 5/2007 |
| WO | WO2007/052155 | 5/2007 |

OTHER PUBLICATIONS

Katz et al., J. Gen. Virol., 1992, 73: 1159-1165.*
Jonge et al., European Journal of Pharmaceutical Sciences, on line Jun. 2, 2007, 32: 33-44.*
Alymova et al., "Immunogenicity and Protective Efficacy in Mice of Influenza B Virus Vaccines Grown in Mammalian Cells or Embryonated Chicken Eggs" 1998, J Virol, 72(5): 4472-4477.
Amacker et al, "Peptide-loaded chimeric influenza virosomes for efficient in vivo induction of cytotoxic T cells." 2005, Int Immunol 17(6):695-704.
Ball, "Quantitation of proteins by elution of Coomassie brilliant blue R from stained bands after sodium dodecyl sulfate-polyacrylamide gel electrophoresis." 1986, Anal. Biochem. 155(1):23-27.
Böttcher et al., "Concentrating traces of copper from 1 M ammonium chloride." 1961, Anal. Chim. Acta. 24:202-203.
Brühl et al, "Humoral and cell-mediated immunity to vero cell-derived influenza vaccine." 2000, Vaccine 19(9-10):1149-1158.
Bungener et al. "Virosomes in vaccine development: induction of cytotoxic T lymphocyte activity with virosome-encapsulated protein antigens." 2002, J Liposome Res 12:155-163.
Felnerova et al. "Liposomes and virosomes as delivery systems for antigens, nucleic acids and drugs." 2004, Curr Opin Biotechnol. 15(6):518-29.
Gerhard, "The analysis of the monoclonal immune response to influenza virus. II. The antigenicity of the viral hemagglutinin." 1976, J. Exp. Med. 144:985-995.
Glück et al, "Influenza virosomes as an efficient system for adjuvanted vaccine delivery." 2004, Expert Opin Biol Ther. 4(7):1139-45.
Glück et al., "Immunogenicity of new virosome influenza vaccine in elderly people." 1994, Lancet 344:160-163.
Glück et al., "Safety and immunogenicity of intranasally administered inactivated trivalent virosome-formulated influenza vaccine containing *Escherichia coli* heat-labile toxin as a mucosal adjuvant." 2000, J. Infect. Dis. 181:1129-1132.
Govorkova et al., "Growth and immunogenicity of influenza viruses cultivated in Vero or MDCK cells and in embryonated chicken eggs." 1999, Dev Biol Stand 98:39-51.
Kumar et al., ""Universal" T helper cell determinants enhance immunogenicity of a *Plasmodium falciparum* merozoite surface antigen peptide." 1992, J. Immunol. 148:1499-1505.
Mischler et al., "Inflexal V a trivalent virosome subunit influenza vaccine: production." 2002, Vaccine 20:B17-23. Nerome et al., "Evaluation of Immune Responses to Inactivated Influenza Vaccines Prepared in Embryonated Chicken Eggs and MDCK Cells in a Mouse Model" 1999, Dev Biol Stand 98:53-63.
Palache et al., "Immunogenicity and reactogenicity of influenza subunit vaccines produced in MDCK cells or fertilized chicken eggs." 1997, J. Infect.Dis 176 Suppl 1:S20-3.
Pöltl-Frank et al., "Use of reconstituted influenza virus virosomes as an immunopotentiating delivery system for a peptide-based vaccine" 1999, Clin Exp Immunol 117:496-503.
Schoen et al., "Gene transfer mediated by fusion protein hemagglutinin reconstituted in cationic lipid vesicles" 1999, Gene Ther 6:823-32.
Smit et al., "Liposomes as target membranes in the study of virus receptor interaction and membrane fusion." 2003, Methods in Enzymology 374-392.

(Continued)

*Primary Examiner* — Ileana Popa
(74) *Attorney, Agent, or Firm* — Riverside Law LLP

(57) ABSTRACT

The present invention relates to virosomes comprising hemagglutinin (HA) with improved fusion activity. Preferably, the HA comprised in said virosomes was derived from influenza virus produced in a cell line. The present invention also relates to compositions and a kit comprising the virosomes according to the invention. Further, the present invention relates to uses and methods involving said virosomes, as well as to a method for preparing same.

18 Claims, 5 Drawing Sheets

OTHER PUBLICATIONS

Stegmann et al. "Membrane fusion activity of influenza virus. Effects of gangliosides and negatively charged phospholipids in target liposomes." 1989, Biochemistry 28:1698-1704.

Struck et al., "Use of resonance energy transfer to monitor membrane fusion." 1981, Biochemistry. 20(14): 4093-9.

Tsurudome et al., "Lipid interactions of the hemagglutinin HA2 NH2-terminal segment during influenza virus-induced membrane fusion." 1992, J. Biol. Chem. 267:20225-20232.

Wood et al., "Application of an Improved Single-Radial-Immunodifusion Technique for the Assay of Haemagglutinin Antigen Content of Whole Virus and Subunit Influenza Vaccines" 1977, Dev Biol Stand. 39:193-200.

Huckriede et al., "The virosome concept for influenza vaccines." 2005, Vaccine 23:S26-S38.

Gray, et al., "Structural studies on membrane-embedded influenza hemagglutin and its fragments," *Protein Science*, 1977, 6:1993-2006.

* cited by examiner

FIGURE 2

FIGURE 3
A
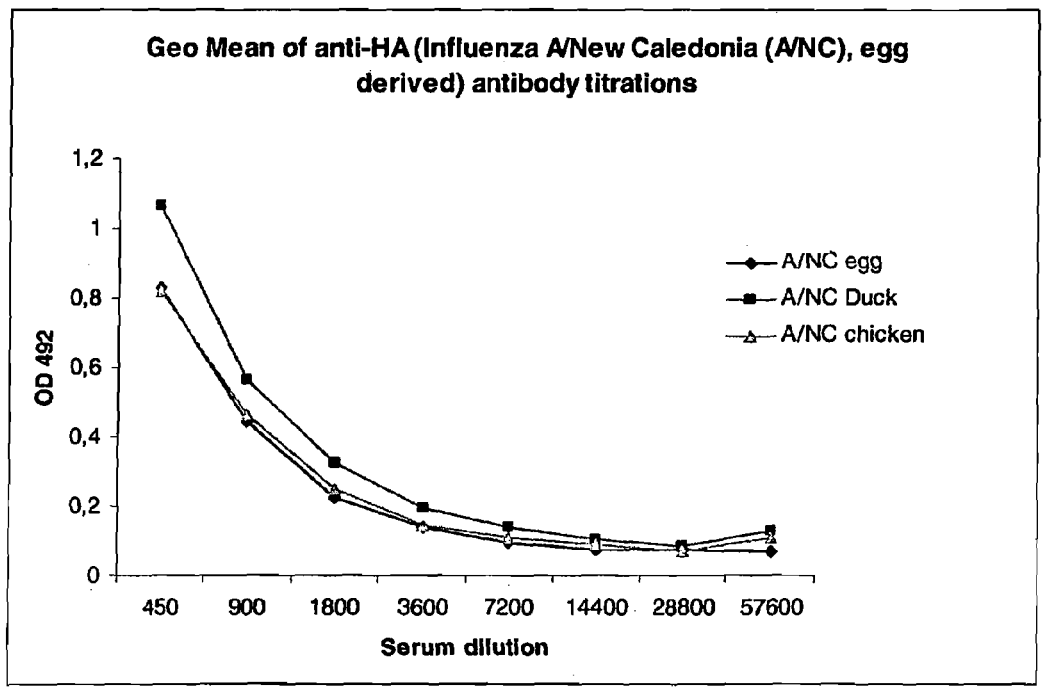
B
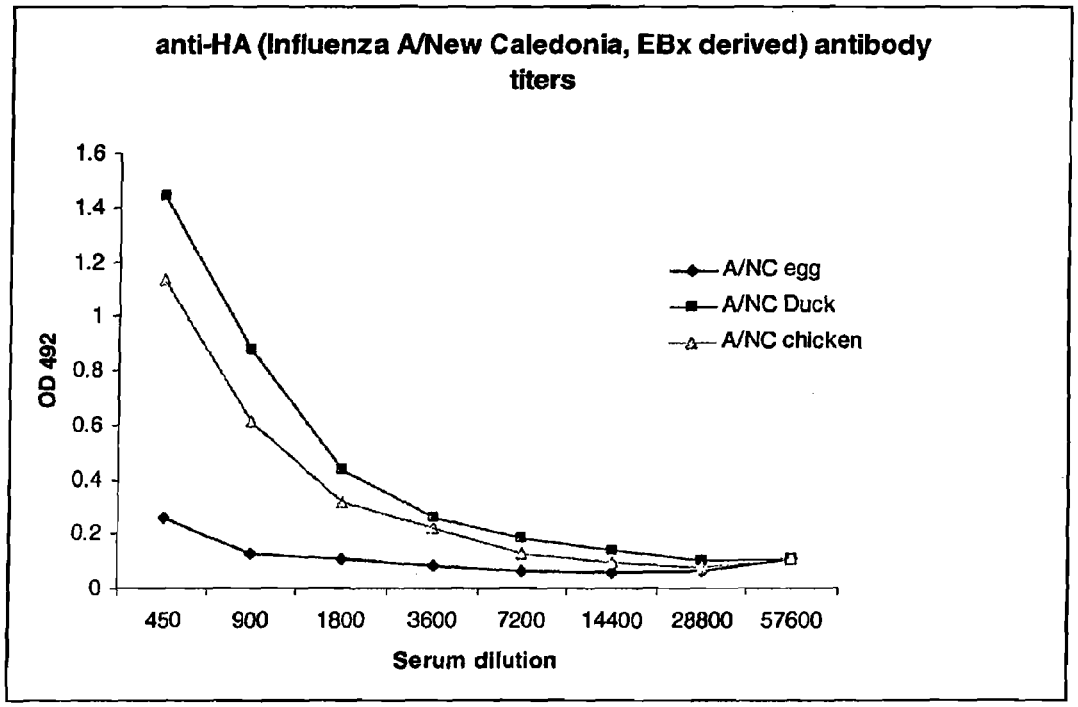

VIROSOMES COMPRISING HEMAGGLUTININ DERIVED FROM AN INFLUENZA VIRUS PRODUCED IN A CELL LINE, COMPOSITIONS, METHODS OF MANUFACTURING, USE THEREOF

CROSS-REFERENCE TO RELATED APPLICATIONS

This is a U.S. National Stage application of PCT International Application No. PCT/EP2008/004780, filed Jun. 13, 2008, which in turn claims the benefit pursuant to 35 U.S.C. §119(a) and §365(b) of European Patent Application No. EP07012283.3, filed on Jun. 22, 2007, each of which are hereby incorporated by reference in its entirety herein.

FIELD OF THE INVENTION

The present invention relates to the fields of immunology and vaccinology. Specifically, the invention relates to improved virosomes, compositions comprising same and uses thereof.

BACKGROUND OF THE INVENTION

One of the paramount goals of medical care is the development of modern vaccines for prophylaxis and efficient delivery of therapeutic substances for the treatment of diseases. So far, virosomes are known as suitable vesicles for antigen-delivery and/or as carrier for therapeutic substances.

Virosomes are complexes composed of lipids and at least one viral envelope protein, produced by an in vitro procedure. The lipids are either purified from eggs or plants or produced synthetically, and a fraction of the lipids originates from the virus providing the envelope protein. Essentially, virosomes represent reconstituted, empty virus envelopes devoid of the nucleocapsid including the genetic material of the source virus(es). Virosomes are not able to replicate but are pure fusion-active vesicles. These virosomes are functional in that their membrane fusion activity closely mimics the well defined low-pH-dependent membrane fusion activity of the intact virus, which is solely mediated by the viral fusion protein. Like viruses, virosomes are rapidly internalized by receptor-mediated endocytosis or fusion with the cell membrane.

Mostly, the virosomes utilized are virosomes termed immunopotentiating reconstituted influenza virosomes (IRIVs). IRIVs are spherical, unilamellar vesicles with a mean diameter of 150 nm and comprise a double lipid membrane, consisting essentially of phospholipids, preferably phosphatidylcholines (PC) and phosphatidylethanolamines (PE). IRIVs contain the functional viral envelope glycoproteins hemagglutinin (HA) and neuraminidase (NA) intercalated in the phospholipid bilayer membrane. The biologically active HA does not only confer structural stability and homogeneity to virosomal formulations but also significantly contributes to the immunological properties by maintaining the fusion activity of a virus. Optionally, the IRIVs comprise hemagglutinin molecules of more than one virus strains, thus forming chimeric IRIVs.

IRIVs have been developed by incorporating the hemagglutinin (HA) from an influenza A strain into liposomes composed of phosphatidylcholin. The influenza virus surface glycoprotein HA guides the virosomes specifically to antigen-presenting cells and leads to fusion with their endosomal membrane. This process provides optimal processing and presentation of the antigens to immunocompetent cells. The T lymphocytes are activated to produce cytokines which in turn stimulate the B lymphocytes to form large amounts of specific antibodies. Moreover, the stimulation of B lymphocytes also occurs through direct contact with the antigen-virosome complex.

Virosomes are highly effective adjuvant/carrier systems in modern vaccination/therapy, possessing superior properties as antigen delivery vesicles and a strong immunogenic potential whilst concomitantly minimizing the risk of side effects. Moreover, virosomes show adjuvant (WO92/19267), trans-adjuvant (European patent application EP05027624) and a non-specific immune stimulating effect (European patent application EP06027120).

For more than 50 years, influenza vaccines have been produced in embryonated chicken eggs. However, the conventional standard methodology is extremely lengthy and cumbersome. Current egg-derived vaccine production requires up to nine months from the isolation of a newly identified virus strain to the final product. This may hinder the response to unanticipated demands such as the discovery of pandemic strains, production failures and seasonal influenza virus strain changes. Moreover, the traditional egg-based methodology requires a huge amount of eggs, an adaptation of the virus isolate to the egg and an extensive purification to reduce the amount of contaminating egg proteins and to minimize the risk of allergies against egg albumins.

In contrast, a cell line-based process is faster and more flexible with respect to virus propagation and allows the production of strains that cannot be adequately grown in eggs (e.g. Avian Hong Kong Flu in 1997). Moreover, the use of cell lines for manufacture of viruses has several advantages in connection with the safety of the resulting vaccine: no antibiotic additives are present in the vaccine formulation; no toxic preservatives (such as thiomersal) are needed; endotoxin levels are reduced, no egg allergy may be caused; growth takes place in protein and serum free media (no adventitious agent/BSE); the virus vaccine preparations are of high purity.

Recently, there have been considerable efforts to develop cell culture systems for vaccine production. Most of the known cell culture systems are based on mammalian cell lines such as e.g. Vero cells, MDCK cells, BHK cells and PerC6 cells. There have been a number of reports on vaccine development based on mammalian cell culture systems. However, virus vaccines produced in said mammalian cell culture systems suffer from the risk of autoimmune reactions to mammalian cell-derived proteins.

The virosome fusion process is essential for an efficient antigen/drug delivery (Schoen P, et al., 1999). Therefore, there is a need in the art to develop virosomes with improved quality with respect to their fusogenic activity and immunogenicity.

SUMMARY OF THE INVENTION

The present invention fulfils this need by the provision of novel virosomes that comprise hemagglutinin (HA) derived from influenza viruses produced in avian cell lines. These new virosomes are characterized by both an improved fusion activity and an improved immunogenicity in comparison to virosomes comprising hemagglutinin derived from influenza viruses produced by the standard procedure using chicken eggs.

Thus, in a first aspect, the invention relates to a virosome comprising hemagglutinin, wherein the hemagglutin was derived from influenza virus produced in an avian cell line.

An "avian cell line" within the meaning of the present invention is a cell culture selected for uniformity from a cell population derived from a usually homogeneous avian tissue source (as an organ). The term excludes avian eggs, such as chicken eggs. Hence, "HA derived from influenza virus produced in an avian cell line" means that the HA is derived from viruses grown in a cell culture originating from an avian tissue, rather than being derived from viruses grown on eggs. Preferred avian cell lines include, without limitation, primary cell lines such as Chicken Embryo Fibroblasts (CEF); permanent/immortalized cell lines, e.g. DF-1 (U.S. Pat. No. 5,672, 485), PBS (U.S. Pat. No. 5,989,805), and HD11.

Moreover, the invention relates to a virosome comprising hemagglutinin, wherein the fusion activity of said virosome is at least 50% higher compared to the fusion activity of a virosome comprising HA derived from influenza viruses that were produced on chicken eggs and that has the same primary structure or peptide sequence. In a preferred embodiment, the virosome according to the invention further has an immunogenicity which is significantly higher compared to the immunogenicity of a virosome comprising HA that was derived from influenza viruses produced on chicken eggs. Preferably, the virosome according to the invention has a fusion activity which is at least 30% higher compared to the fusion activity of a virosome comprising HA that was derived from influenza viruses produced in mammalian cells.

Surprisingly, it has been found that the quality of the fusogenic activity of virosomes depends on the process for production of the influenza virus from which virosomes are reconstituted. In a preferred embodiment, the HA comprised in the virosome according to the invention was derived from influenza viruses produced in a cell line. Preferably, the HA was derived from influenza viruses produced in an avian cell line.

A patent application by Vivalis (WO2006/108846) relates to use of avian embryonic stem cells, preferably the EBx cell line, for the production of viral vectors and viruses. However, WO2006/108846 does neither disclose nor suggest the use of HA obtained from cell line-derived viruses in virosomes.

The virosome may be a chimeric virosome, wherein the HA is derived from at least two different influenza virus strains. Moreover, the virosome may be lyophilized. In a preferred embodiment of the invention, the virosome is loaded with an antigen. In a further preferred embodiment, the virosome according to the invention is naked/empty.

In another aspect, the invention relates to compositions comprising a virosome according to the invention. In a preferred embodiment, the composition is a vaccine. In another preferred embodiment, the composition is immunogenic and further comprises a liposome and at least one antigenic molecule. Preferably, the at least one antigenic molecule is entrapped in the liposome.

In a further aspect, the invention relates to the use of the virosome according to the invention as an antigen delivery vehicle in a pharmaceutical composition to generate an immune response against an antigen of various origins. The virosomes according to the invention may also be used for preparing a pharmaceutical composition for vaccination or immunization. Moreover, the present invention relates to immunostimulatory virosomes devoid of loaded antigens. Accordingly, the invention relates to the use of the virosome according to the invention as a non-specific immunostimulating agent for preparing pharmaceutical compositions to generate efficient immune responses against antigens of various origins. Finally, the invention relates to the use of the virosome according to the invention for preparing a pharmaceutical composition for treating or preventing a disease or disorder.

In yet another aspect, the present invention relates to a kit comprising a virosome or a composition according to the invention.

A further aspect involves a method for the vaccination or immunization of a subject with the virosome or the composition according to the invention, comprising administering said virosome or said composition to a subject to elicit an immune response. Also encompassed by the present invention is a method for the treatment or prevention of a disease or disorder (such as an infectious diseases and/or cancer) in a subject in need thereof with the virosome or the composition according to the invention, comprising administering said virosome or said composition to said subject.

In a further aspect, the present invention relates to a method for the preparation of a virosome according to the invention, comprising the steps of treating a whole influenza virus with a detergent or short chain phospholipid, separating the HA containing fraction and removing the detergent, resulting in the reconstitution of the virosome. Alternatively, the separation step may comprise the addition of phospholipids. The present invention also relates to a virosome obtainable by said method.

BRIEF DESCRIPTION OF THE DRAWINGS

FIG. 2 shows the fusion activity of influenza virosomes. Upper panel: Graphic representation of the fusion activity results illustrated in table 2, Experiment 2, Example 4.5. Lower panel: Ratios of fusion activity of cell- vs. egg-derived influenza virosomes. Bars represent average ratios between samples at different dilution steps representing HA concentrations between 1 and 6 µg HA in a total volume of 0.8 ml).

FIGS. 3 and 4 show the results of immunogenicity studies in mice. As can be seen in FIG. 4, there is improved immunogenicity of virosomes comprising HA derived from influenza virus produced in an (avian) cell line and loaded with heterologous antigen (UK39). FIG. 3A shows that the origin of the virus (cell line/cell culture or egg) used to prepare the virosome of the invention has no significant influence on the antibody titers against egg-derived HA after one immunization. FIG. 3B shows that there is an improved immunogenicity of HA: higher antibody titers against EBx-derived HA after the first immunization with virosomes formulated with HA derived from viruses produced in EBx cells. FIG. 4 shows individual titers of antibodies directed against the heterologues antigen UK39. This is done by calculating the dilution corresponding to the OD value 20% of the maximum OD-value of the control-serum included on each plate. In the example shown, the differences observed between virosomes comprising HA derived from virus produced on eggs and virosomes comprising HA derived from virus produced in cell lines with respect to the immunogenicity of heterologous antigen UK39 are significant: p=0.002 for chicken cell culture vs. egg and p=0.009 for duck cell culture vs. egg using Wilcoxon testing.

DETAILED DESCRIPTION OF THE INVENTION

Definitions

Figure 1:
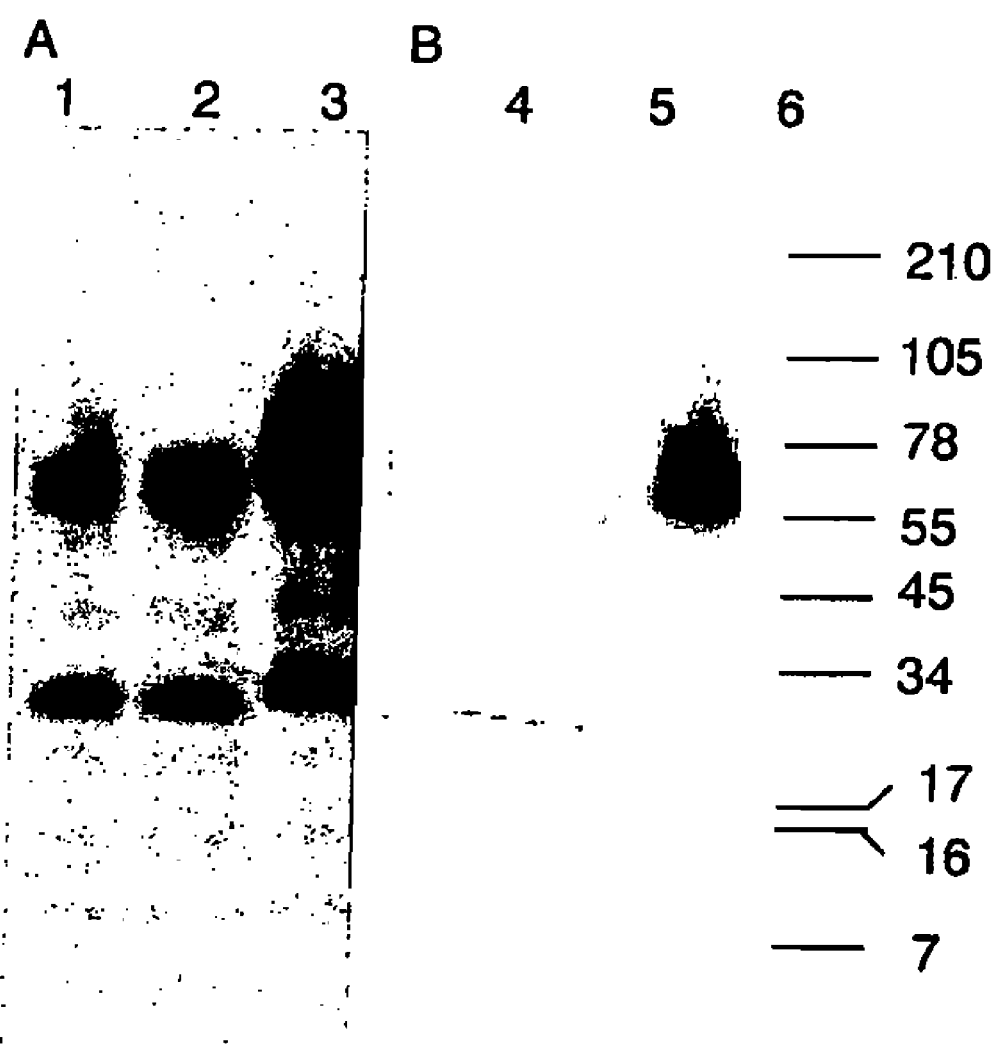
FIG. 1 shows a western blotting analysis of virosomal preparations using hemagglutinin from Influenza A/New Caledonia infected chicken cell line (lanes 1 and 4), duck cell line (lane 2 and 5) or virus derived from propagation on embryonated eggs (lanes 3 and 6). Blot A was developed using an influenza A specific polyclonal rabbit serum, blot B was developed using a monoclonal antibody recognizing a specific epitope on the hemagglutinin subunit HA1.

As used herein the term "virosome" refers to a vesicle produced by an in vitro procedure that is composed of lipids and at least one viral envelope protein. The lipids are either purified from a biological origin (e.g. eggs, plants, animals, cell cultures, bacteria, viruses) or produced synthetically (chemical synthesis). A virosome may be a reconstituted viral envelope which can be derived from a variety of viruses and which lacks the infectious nucleocapsids and the genetic material of the source virus, e.g. an immunopotentiating reconstituted influenza virosome (IRIV). Thus, a virosome is a special type of lipid vesicle comprising, in its lipid membrane, at least one viral envelope protein. As used herein, the term "viral envelope protein" refers to any protein encoded by an enveloped virus from which the virosome of the invention is partly or completely derived and that is present in the virosomal lipid membrane. Viral envelope proteins sometimes function as "viral fusion proteins", when they play a role in the fusion of viruses or virosomes with target cell membranes.

The virosome of the invention may comprise more than one type of envelope protein. Said additional proteins comprised in the membrane of the virosome are not necessarily derived from enveloped viruses but may originate from any living organism (including microorganisms such as bacteria, fungi, or parasites).

The envelope protein(s) may be recombinant proteins, provided that the biochemical properties of the protein allow its physical attachment to a lipid membrane. These envelope proteins account for the virosomal functionality.

In contrast to viral systems, virosomes are safe, since the infectious nucleocapsid of the virus has been removed. So far, virosomes are mainly used as vaccines by incorporating antigen onto the surface or into the lumen of the virosomes. In contrast to virus-like particles (VLPs), virosomes do not form spontaneously upon recombinant expression of the protein in an appropriate expression system but are the result of a controlled in vitro process, which allows large-scale industrial production of virosomes.

As used herein, the term "antigen delivery vehicle" refers to a virosome containing in its lumen or incorporated in its membrane or associated with its surface at least one disease-specific antigen.

As used herein, the term "fusion activity" refers to the ability of a virosome to fuse with a cellular and/or synthetic membrane. While in vivo, virosomes either, fuse with the outer cell membrane or the endosomal membrane, the fusion with liposomes is a recognized model system to determine the fusion activity of virosomes in vitro (Smit J M et al, 2003). It was demonstrated that the fusion of influenza virus and virosomes with liposomes has similar characteristics as the fusion with the biological target membranes (Stegmann T. et al. 1989).

As used herein, the term "cellular membrane" refers to a biological membrane that occurs naturally in cells, such as the outer membrane of a cell or the membrane of an endosome contained in a cell. In contrast, the term "synthetic membrane" refers to an artificial membrane, such as the lipid membrane of a liposome. An example of a synthetic membrane is the liposomal membrane consisting of phosphatidyl-cholin (PC) and DPPG (di-palmityl-phosphatidyl-glycerol) only and lacking proteins which are typically comprised in cellular membranes.

The fusion activity of viruses and virosomes is generally evaluated by a fluorescence resonance energy transfer (FRET) assay (Struck D K et al, 1981). This assay describes a photophysical process that causes quenching of the fluorescence of one species (the donor) by nonradiative transfer of its excitation energy to another species (the acceptor). It is essential that the emission spectrum of donor overlaps the absorption spectrum of the acceptor. The quenching effect is strictly dependent on the distance between the two molecules: every event inducing some changes in the molecular proximity promotes dequenching and consequently release of energy, which can be monitored. Thus, FRET represents a valuable in vitro test for investigating many biological phenomena such as fusion between virus particles and biological cell membranes. Different fusion assays based on FRET have been developed to demonstrate the in vitro fusion activity of viral membranes (viruses or virosomes) with liposomes or ghost erythrocytes (Smit J M et al, 2003). Some of these assays include labeling of the target membranes (liposomes), others the labeling of the test sample, namely virus or virosomes. However, the need to label the test sample is not compatible with cGMP compliant quality control of pharmaceutical products. A more sensitive fusion assay based on FRET that avoids the labeling of the test sample has been developed by Pevion Biotech (Amacker M. et al, 2005;).

The fusion activity of the virosomes according to the invention may be measured by a FRET assay as described in the Examples below. To determine whether the fusion activity of a virosome according to the invention is increased in comparison to another virosome, the following steps are carried out: (a) measuring the fusion activities of both a virosome comprising different amounts of HA derived from viruses produced in a cell line and a corresponding virosome comprising the same amounts of HA derived from viruses produced on eggs, (b) identifying the ratio of the fusion activities of (a) (i.e. virosome comprising the cell-derived HA versus the corresponding virosome comprising the egg-derived HA), and (c) averaging the resulting ratios. Thus, to compare the fusion activities, multiple measurements with different amounts of HA are required for each type of virosome. In a preferred embodiment, the fusion activity is determined with virosomes comprising HA in the range of 3-6 μg in a total volume of 0.8 ml. For an example of calculation, see section 4.5 of the Examples below. The fusion of a given virosome is "50% higher", if the mean ratio determined as outlined above yields a value $\geq 1.5$.

As used herein, the term "immunogenicity" refers to the ability of a particular substance (antigen) to provoke an immune response. To determine whether the immunogenicity of a virosome according to the invention is significantly higher (i.e. improved), a subject is immunized with the virosome or composition according to the invention comprising HA or HA in combination with a further specific (heterologous) antigen, and the antibody titer against HA or said antigen in the serum of said subject is recorded. For comparison, another subject is immunized with corresponding virosomes or composition comprising HA derived from viruses produced on eggs. The immunogenicity of a virosome is "significantly improved" or "significantly higher" if the Wilcoxon test carried out on the antibody titers elicited by the virosome according to the invention (comprising HA derived from virus produced in a cell line) compared to the corresponding virosomes or composition comprising HA derived from virus produced on eggs yields a p value which is lower than 0.05. For an example of calculation, see section 5.1 of the Examples below.

The terms "cell line-derived", "derived from a cell line" and "produced in a cell line" are used interchangeably and mean that something is derived from or was produced in a cell line, or cell culture.

As used herein, the term "loaded with antigen" means that the virosome comprises an additional antigen other than HA (that is, a "heterologous antigen" or "non HA antigen"). The antigen may be incorporated into the virosome (e.g. contained in its lumen), absorbed to/bound to the surface of the virosome, integrated into the lipid membrane of the virosome, and the like. A virosome loaded with antigen may be used as an antigen delivery vehicle.

As used herein, the term "chimeric virosome" refers to a virosome that contains hemagglutinin from at least two different influenza virus strains.

As used herein, the terms "empty" and "naked" are used interchangeably with reference to virosomes, and refer to the fact that the so-characterized virosomes contain no disease-specific antigen in their lumen, nor do they bear any in their lipid bilayer. As such, a "naked" or "empty" virosome contains nothing but the surrounding solution in its lumen, and no protein except for the viral envelope protein HA and possible traces of neuraminidase (NA) in its lipid membrane.

As used herein, the terms "therapeutic", "therapy" and the like refer to action taken against a disease or disorder which has already been contracted, or which is suspected of already having been contracted, regardless of whether any corresponding symptoms have already set in. As such, "therapy" and "therapeutic" refer to the elimination of a disease or disorder or at least amelioration of the symptoms thereof in a subject such that, if symptoms are already present, these are mitigated or, if no symptoms are yet present, the onset of such symptoms is lessened in severity or excluded altogether. As used herein, the term "prophylactic", "prophylaxis", "prevent", "prevention" and the like refers to action taken to prevent a subject from contracting a disease, when a subject is not suspected of having contracted the disease in the past, but there exists an expectation that the subject is or will be in danger of contracting a particular disease or disorder in the present or future. Furthermore the terms refer to action taken to prevent a subject from contracting a disease, when a subject has already received a vaccination/immunization, the effect of which, however, is not long-lasting.

As used herein, the term "pharmaceutical" refers to characteristics of compositions and/or medicaments which render them suitable for administration to a living animal, preferably a human.

As used herein, the terms "potentiating", "immunopotentiating", "stimulating", "immunostimulating", "immunostimulatory" and the like are used interchangeably to refer to a compound or enhancing effect on immune functions which may lead to destruction or clearance of antigen-bearing pathogens or malignancies, and/or to immunity thereto.

As used herein, the terms "non-specific", "unspecific" and the like refer to the general immunostimulatory activity of the claimed virosome, meaning that the immune system is potentiated in its ability to prevent, combat and/or eliminate any one of many diseases or disorders rather than just a single disease or disorder. Conversely, specific immunostimulatory activity refers to the stimulation of the immune system to prevent, combat and/or eliminate a specific disease or disorder. For example, vaccination against a particular disease is an example of eliciting a specific immunostimulatory activity.

As used herein, the terms "disease" and "disorder" refer to an abnormality of the body or mind that causes discomfort, dysfunction, or distress and is classified into infectious, non infectious, neoplastic, immune or metabolic disorder or disease.

Influenza Viruses

Influenza viruses (Orthomyxoviridae) are enveloped negative-strand RNA viruses with a segmented genome. They are divided into two genera: one including influenza A and B and the other consisting of influenza C, based on significant antigenic differences between their nucleoprotein and matrix proteins. The three virus types also differ in pathogenicity and genomic organization. Type A is found in a wide range of warm blooded animals, types B and C are predominantly human pathogens. Influenza A viruses are further subdivided by antigenic characterization of the hemagglutinin (HA) and neuraminidase (NA) surface glycoproteins that project from the surface of the virion. There are currently 15 HA and nine NA subtypes. Influenza A viruses infect a wide variety of animals, including birds, swine, horses, humans and other mammals. Aquatic birds serve as the natural reservoir for all known subtypes of influenza A and probably are the source of genetic material for human pandemic influenza strains.

Influenza viruses accumulate point mutations during replication because their RNA polymerase complex has no proofreading activity. Mutations that change amino acids in the antigenic portions of surface glycoproteins may give selective advantages for a viral strain by allowing it to evade preexisting immunity. The HA (hemagglutinin) is the major antigenic determinant of influenza virus, inducing and binding neutralizing antibodies. The HA molecule initiates infection by binding to receptors (sialic acid residues) on certain host (respiratory) cells.

The HA molecule consists of two distinct domains, a stem structure protruding from the virion surface consisting of the HA2 and part of HA1 of the HA polypeptide and a globular head which is composed entirely of HA1.

Antibodies against the HA protein prevent receptor binding and are very effective at preventing re-infection with the same strain. HA can evade previously acquired immunity by either antigenic drift, in which mutations of the currently circulating HA gene prevent antibody binding, or antigenic shift, in which the virus acquires HA of a new subtype. These changes also accumulate to a greater extent in HA than NA. Changes in other influenza proteins occur more slowly. Likewise, antigenic drift pressure is greatest in human-adapted influenza strains, intermediate in swine- and equine-adapted strains, and least in avian-adapted strains.

Influenza strains can be characterized genetically by sequence comparison of the individual gene segments.

Whilst work continues with development of vaccines against annual epidemic influenza strains, the world is preoccupied with the threat of an influenza pandemic. Health and regulatory authorities throughout the world are currently engaged in developing strategies in order to be prepared for a pandemic influenza.

Virosomes

The virosomes according to the invention may be used to deliver a substance (e.g. an immunogenic molecule, a drug and/or a gene) to a target cell. Unlike liposomes, virosomes offer the advantage of efficient entry into the cells triggered by the viral envelope protein, followed by the intracellular release of the virosomal contents. Moreover, if certain active viral envelope proteins are incorporated into their membranes, the virosomes may release their contents into the cytoplasm immediately after fusion with a cell membrane, e.g. hereby preventing the degradation of the therapeutic substance in the acidic environment of the endosome.

The virosomes according to the invention are especially useful in the field of vaccination, where it is desired to stimulate an immune response to an antigen associated with a particular disease or disorder. In such cases, the antigen is typically encapsulated in or bound to the virosome, which then delivers this antigen to the host immune system to be vaccinated. By virtue of the particular antigen delivered, the resulting prophylactic and/or therapeutic is necessarily specific for the disease or disorder with which the antigen is associated.

The virosomes can further be loaded simultaneously with several different B-cell and T-cell epitopes (Pöltl-Frank et al. (1999)), including universal T-helper cell epitopes (Kumar et al. (1992)) and others known to those of skill in the art. Thus, virosomes are highly effective adjuvants in modern vaccination, possessing superior properties as antigen delivery vehicles and a strong immunogenic potential while concomitantly minimizing the risk of side effects.

Immunopotentiating reconstituted influenza virosomes (IRIVs) are functional, in that their membrane fusion activity closely mimics the well-defined low-pH-dependent membrane fusion activity of the intact virus, which is solely mediated by the viral envelope protein. Like viruses, influenza virosomes are rapidly internalized by receptor-mediated endocytosis or opsonization. In contrast to viral systems, virosomes are safe, since the infectious nucleocapsid of the virus has been removed. Thus, the virosomes according to the invention represent a promising carrier system for the delivery of a wide variety of different substances, either encapsulated in their aqueous interior or co-reconstituted in their membranes. Co-reconstitution of different receptors within the virosomal membrane, furthermore, allows the targeting of virosomes to different cells or tissues. Virosomes are mainly used as vaccines by adding antigen onto their surface or by encapsulating antigen in the virosomal lumen or by making use of their adjuvant effect when administered in combination with antigen-loaded liposomes.

IRIVs are reconstituted from influenza virus envelopes and use the same cell receptor-mediated endocytosis as their viral counterparts. The receptor binding and the membrane fusion activity of influenza virus with endosomes are known to be mediated by the major viral envelope glycoprotein HA (Bungener et al. (2002)). Similar to viral vectors, the mildly acidic pH in the lumen of endosomes triggers the fusion of virosomal with endosomal membranes and thus the release of encapsulated material such as DNA, RNA, or proteins into the cytosol of the cells. Therefore, exogenous antigens encapsulated in virosomes may access the MHC class I pathway without the need of de novo protein synthesis. Proteins displayed on the surface of the virosomes remain in the endosomal compartment upon fusion and therefore are thought to become available for the MHC class II pathway.

Commercially available virosomal vaccines (INFLEXAL® V, EPAXAL®) have been shown to be very efficacious and safe (Glück et al.(2000)). The potential of virosomes as a delivery system has been demonstrated for nucleic acids and peptide-based vaccines, e.g., for malaria (Pöltl-Frank et al. (1999)). Recent reports also concluded that synthetic peptide vaccines administrated s.c. with virosomes were able to induce a strong CTL immunity (Amacker et al. (2005)).

Preparation of Virosomes

The preparation of virosomes is well-known to the person skilled in the art. Suitable protocols for the preparation of virosomes are described, for example, in EP 538437 and in Mischler and Metcalfe (2002).

The virosomes according to the invention may be reconstituted from original viral membrane lipids and spike glycoproteins after solubilization of influenza virus with octaethyleneglycol monododecyl ether, sedimentation of the nucleocapsid (the viral glycoproteins and lipids will remain in the supernatant), and removal of the detergent in the supernatant with a hydrophobic resin (Bio-Beads SM2). Protocols for the preparation of influenza virosomes are given in WO 92/19267 and for generic virosomes in WO 04/071492.

The preparation of virosomes containing HAs from different strains of influenza viruses may be performed with equal amounts of proteins of those viruses solubilized with the non-ionic detergent octaethyleneglycol monododecyl ether. After removal of the detergent with Bio-Beads SM2, virosomes containing different types of envelope proteins may be formed. The protocol to prepare virosomes from either egg-derived material or cell line-derived material is identical.

Influenza virus subtypes from which the virosomes according to the present invention may be derived are influenza H1N1, influenza H1N2, influenza H2N2, influenza H3N2, influenza H3N8, influenza H5N1, influenza H5N2, influenza H5N3, influenza H5N8, influenza H5N9, influenza H7N1, influenza H7N2, influenza H7N3, influenza H7N4, influenza H7N7, influenza H9N2 and/or influenza H10N7. Further, the at least one viral envelope protein may be derived from influenza A/Bangkok/1/79, influenza A/Beijing/32/92, influenza A/Brazil/11/78, influenza A/California/7/2004 (H3N2), influenza A/Chile/1/83, influenza A/Christchurch/4/85, influenza A/England/42/72, influenza A/Fujian/411/2002 (H3N2), influenza A/Guizhou/54/89, influenza A/Hong Kong/1/68, influenza A/Johannesburg/33/94, influenza A/Leningrad/360/86, influenza A/Mississippi/1/85, influenza A/Moscow/10/99 (H3N2), influenza A/New Caledonia/20/99 (H1N1), influenza A/Panama/2007/99-RESVIR-17), influenza A/Philippines/2/82, influenza A/Port Chalmers/1/73, influenza A/Scotland/840/74, influenza A/Shangdong/9/93, influenza A/Shanghai/11/87, influenza A/Sichuan/2/87, influenza A/Singapore/6/86, influenza A/Sydney/5/97, influenza A/Texas/1/77, influenza A/USSR/90/77, influenza A/Victoria/3/75, influenza A/Wisconsin/67/2005 (H3N2), influenza A/Wuhan/359/95, influenza A/Wyoming/3/2003 X-147), influenza B/Hong Kong/330/2001, influenza B/Jilin/20/2003, influenza B/Malaysia/2506/2004, influenza B/Shanghai/361/2002, influenza A/Beijing/262/95, influenza B/Victoria/98926/70, influenza B/Singapore/222/79, influenza B/USSR/100/83, influenza B/Yamagata/16/88, influenza B/Panama/45/90, influenza B/Hong Kong/5/72, influenza B/Ann Arbor/1/86, influenza A/Bayern/7/95, influenza B/Shangdong/7/97), and/or B/Jiangsu/10/2003.

IRIVs comprise a double lipid membrane, consisting essentially of phospholipids, preferably phosphatidylcholines (PC) and phosphatidylethanolamines (PE). In contrast to liposomes, IRIVs contain the functional viral envelope glycoproteins HA and neuraminidase (NA) intercalated in the phospholipid bilayer membrane. The biologically active HA significantly contributes to the immunological properties by maintaining the fusion activity of a virus.

IRIVs act as efficient and highly effective means of non-specifically enhancing the immune response. They are also known to have an excellent safety profile (Glück et al. (2000)), meaning that they are well suitable for use in medications intended for unspecific immunostimulation in humans.

The virosome of the present invention may also be a chimeric virosome, meaning that it contains viral envelope HA proteins from at least two different influenza virus strains, for example from influenza strains X-31 and A/Sing or any of the virus strains mentioned above. Additionally, other known viral envelope proteins may be used, such as vesicular stomatitis virus (VSV) G protein, Semliki forest virus (SFV) E1 protein, or Sendai virus F protein, or G protein or F protein from Respiratory syncytial virus (RSV) or Hepatitis C virus (HCV) E protein among many others, to construct chimeric virosomes capable of undergoing sequential and separate fusion events.

As shown previously (Tsurudome et al. 1992), HA fusion proteins from different strains of viruses can display markedly different temperature characteristics of fusion and inactivation. For example, about pH 5.0, X-31 HA triggers fusion efficiently at low temperature, whereas at the same pH, HA from PR8/34 or A/Singapore virus requires elevated temperature (>25° C.). Hence chimeric virosomes may contain proteins in their membrane that mediate fusion at two distinct temperatures. Different temperature-sensitivity is a particularly advantageous characteristic of the fusion proteins, as it allows convenient and simple control of fusion reactions. As an example, virosomes containing HA molecules from both X-31 and PR8/34 virions are capable of catalyzing two distinct fusion reactions at pH 5: the first at low temperature (4-10° C.), the second at elevated temperature (>25° C.). However, other fusion proteins with distinct fusion characteristics, including sensitivity to temperature, ion concentration, acidity, cell type and tissue type specificity, etc. are well known in the art.

Fusion proteins with different fusion characteristics can be derived from different influenza strains, such as MRC-11, X-97, NIB24, NIB26, X-47, A/Johannesburg/33 and A/Singapore, to name a few.

The virosome of the present invention preferably comprises lipids selected from the group consisting of cationic lipids, synthetic lipids, glycolipids, phospholipids, cholesterol, or derivatives thereof. Phospholipids preferably comprise phosphatidylcholine, sphingomyelin, phosphatidylethanolamine, phosphatidylserine, phosphatidylglycerol, phosphatidic acid, cardiolipin, and phosphatidylinositol with varying fatty acyl compositions. Cationic lipids are preferably selected from the group consisting of DOTMA (N-[(1-(2,3-dioleyloxy)propyl]-N,N,N-trimethylammonium chloride), DOTAP (N-[1-(2,3-dioleoyloxy)propyl]-N,N,N-trimethylammonium chloride, DODAC (N,N-dioleyl-N,N,-dimethylammonium chloride), DDAB (didodecyldimethylammonium bromide), TC-Chol (cholesteryl N-(trimethylammonioethyl)carbamate chloride), DC-Chol (cholesteryl N-(dimethylammonioethyl)carbamate chloride); or other cationic cholesterol derivatives, and stearylamine or other aliphatic amines, DPPE (dipalmitoylphosphatidylethanolamines), DOGS (Dioleoyl-Glycero-Succinate), DOSPA (2,3-dioleoyloxy-N-[2(sperminecarboxamido)ethyl]-N,N-dimethyl-1-propanaminium trifluoroacetate), DOSPER (1,3-dioleoyloxy-2-(6-carboxyspermyl)propylamide), THDOB (N,N,N',N'-tetramethyl-N,N'-bis (2-hydroxyethyl)-2,3,-dioleoyloxy-1,4-butanediammonium iodide), DOPA (Dioleoyl-sn-Glycero-Phosphate), DOTP (dioctyl tere-phthalate), DOSC (dioleoyl-succinyl-glycerol), DOTB (dioleoyl-e-(4'-trimethylammonio)-butanoyl-sn-glycerol), DOPC (Dioleoyl-sn-Glycero-Phosphocholine) and the like. Especially preferred, the cationic lipid is chosen from cationic cholesterol derivatives such as TC-Chol (cholesteryl N-(trimethylammonioethyl)carbamate) or DC-Chol (cholesteryl N-(dimethylammonioethyl)carbamate).

They may be formulated as small unilameliar liposomes in a mixture with PC (phosphatidylcholine). The virosomes of the present invention may preferably comprise egg-derived PC and, more preferably, 1-oleyl-3-palmitoyl-rac-glycero-2-phosphatidylethanolamine.

The membrane of the virosome of the invention preferably comprises between 1.9 and 37 mol % DC-Chat or TC-Chol, relating to a total lipid content of the membrane. In an especially preferred embodiment, the content of DC-Chol or TC-Chol in the membrane is between 1.9 and 16 mol % of the total lipid content of the membrane. The residual lipid content of the membrane consists preferably of phospholipids, most preferably phosphatidylcholine and phosphytidylethanolamine in a ratio of 4:1.

A co-emulsifying agent may also be used in order to improve the rigidity and/or the sealing of the virosome. Examples of co-emulsifying agents are cholesterol esters charged or neutral as cholesterol sulphate, derivatives with a sterol backbone, such as derivatives from vegetable origin, for example sitosterol, sigmasterol, and mixtures thereof.

A virosome according to the invention may for example be obtained by a process analogous to any one of the processes for making DOTAP-containing virosomes disclosed in Examples 1 to 3 and 6 of WO 97/41834, except that DOTAP is replaced by DOSPER and that the DOSPER concentration in the final virosome membrane is properly adjusted as disclosed in WO 97/41834 and, in particular, does not exceed 30% by weight of the total lipid content of the virosome. Basically, a method of preparation of the present virosomes may comprise the following steps:

a) preparing a buffer solution that comprises a non-ionic detergent and that further comprises DOSPER and other lipids and at least one viral envelope protein;
b) adjusting the lipid concentrations to—based on total membrane lipids—5 to 30% by weight of DOSPER and to a balance of 95 to 70% by weight of said other lipids comprising phosphatidylcholine (PC) or a derivative thereof and optionally phosphatidylethanolamine (PE) and/or cationic lipids other than DOSPER; and
(c) removing the detergent by dialysis or by treating the solution with microcarrier beads, resulting in the formation of said virosomes.

Use of the Virosomes According to the Invention

The virosomes according to the invention may be used in the preparation of medicaments for treating and/or preventing at least one disease or disorder. The (at least one) disease or disorder may be an infectious, a non-infectious, a neoplastic, an immune or a metabolic disease or disorder. In one embodiment, the inventive use entails the application of the virosome of the invention to healthy subjects facing a temporarily increased exposure to one or more infectious diseases or disorders, or of (still) healthy subjects immediately following suspected exposure to one or more infectious diseases or disorders but before appearance of symptoms or confirmation of diagnosis. The classification of an action vis a vis a subject as therapeutic or prophylactic is discussed hereinabove.

The inventive use may also be applied to the treatment of one or more already existing diseases or disorders, optionally as a supplementation of specific treatments of such diseases or disorders.

In one embodiment, the at least one infectious disease or disorder may be a viral disease or disorder, a bacterial disease or disorder, a fungal disease or disorder, a parasitic disease, or disorder or a prionic disease or disorder.

According to a further embodiment the animal is a mammal. The mammal is preferably a human, a chimpanzee, a cynomologous monkey, a gibbon, a simian monkey, a macaque monkey, a mouse, a rat, a cat, a dog, a horse, a rabbit, a camel, a llama, a ruminant, a horse or a pig. A preferred ruminant may be a cow, a bull, a goat, a sheep, a bison, a buffalo, a deer or a stag.

In a further embodiment, the medicament is suitable for administration intramuscularly, intradermally, intravenously (e.g. by injection), subcutaneously, intraperitoneally, parenterally, topically, endotracheally, intraauricularly, intraarticularly, intraocularly, locally, by gargling, by a patch (for example a skin patch), by spray (for example a nasopharyngeal spray) sublingually, orally (e.g. tablets, capsules, caplets, dragees), by suppository (e.g. rectal suppository or vaginal suppository), or by drops (e.g. eye drops). Administration may be in a single dose or, as need dictates, in multiple doses with intervening time intervals as deemed appropriate by the supervising clinician.

Repeated applications of the virosomes according to the invention are conceivable. The combination of the virosomes of the invention with other compounds e.g. adjuvants or immunostimulants may synergistically enhance the overall effect. The amount and type of virosome, the site of stimulation, and co-stimulating signals (infections, exposure to allergens, etc.) define the overall effect. The effect is transient, on the order of hours to weeks. The duration of the effect achieved depends on dose magnitude, dose timing, the route of administration chosen as well as the composition of the medicament administered.

The medicament prepared according to the inventive use is administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The preferred amount of virosome to be administered depends on the disease or disorder to be treated or prevented. Generally, doses ranging from about 1 ng/kg to about 100 mg/kg are believed to be effective, said kilograms referring to body weight of the animal treated. The preferred range is believed to be from about 10 ng/kg to about 10 µg/kg. The absolute amount will depend upon a variety of factors, including the composition selected for administration, whether the administration is in single or multiple doses, and individual patient parameters including age, physical condition, size, weight, and the stage of the disease.

The route and regimen of administration will vary depending upon the stage or severity of the disease or disorder to be treated, and is to be determined by the skilled practitioner. The medicament prepared by the inventive use is suitable for parenteral administration. Here, the medicament comprises virosomes dissolved or suspended in an acceptable carrier, preferably an aqueous carrier. A variety of aqueous carriers may be used, e.g. water, buffered water, 0.4% saline, 0.3% glycine, hyaluronic acid and the like. These compositions may be sterilized by conventional, well known sterilization techniques, or may be sterile-filtered. The resulting aqueous solutions may be packaged for use as they are, or lyophilized, the lyophilized preparation being combined with a sterile solution prior to administration.

The medicament prepared by the inventive use may additionally contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others. Actual methods for preparing parenterally administrable compounds will be known or apparent to those skilled in the art and are described in more detail in for example, Remington: The Science and Practice of Pharmacy ("Remington's Pharmaceutical Sciences") Gennaro A R ed. 20th edition, 2000: Williams & Wilkins PA, USA, which is incorporated herein by reference.

The medicament prepared according to the inventive use can also be administered in such oral dosage forms for example as tablets, capsules (each including timed release and sustained release formulations), pills, powders, granules, elixirs, tinctures, solutions, suspensions, syrups and emulsions, or by injection. For instance, for oral administration in the form of a tablet or capsule, the active drug component can be combined with an oral, non-toxic pharmaceutically acceptable inert carrier such as ethanol, glycerol, water and the like.

Similarly, the medicament prepared according to the inventive use may also be administered intravenously (either by bolus or infusion methods), intraperitoneally, subcutaneously, topically with or without occlusion, or intramuscularly. In preferred embodiments, the medicament prepared according to the inventive use is administered intramuscularly, subcutaneously, intradermally, mucosal or transdermally. All of these forms are well known to those of ordinary skill in the pharmaceutical arts.

The dosage regimen according to which the medicament prepared according to the inventive use is to be administered is selected in accordance with a variety of factors, including for example species, age, weight, sex and medical condition of the patient, the stage and severity of the disease or disorder to be treated, and the particular type of virosome employed. A physician of ordinary skill in the art can readily determine and prescribe the effective amount of the medicament required to prevent, counter, or arrest the progress of a malignancy or infectious disease or disorder. Optimal precision in achieving concentration of drug with the range that yields efficacy either without toxicity or with acceptable toxicity requires a regimen based on the kinetics of the virosome's availability to target sites. This process involves a consideration of the distribution, equilibrium, and elimination of the virosome, and is within the ability of the skilled practitioner and can be addressed with no more than routine experimentation.

In one embodiment, the medicament prepared according to the inventive use may be administered in a single daily dose, or the total daily dosage may be administered in divided doses for example of two, three, or four times daily. In another embodiment, weekly or monthly administrations are foreseen.

The daily dose the medicament prepared according to the inventive use may be varied over a range of 10 ng/kg to about 10 µg/kg of virosomes per adult per day. For oral administration, the medicament prepared according to the inventive use is preferably provided in the form of tablets containing from 0.001 to 1,000 mg, preferably 0.01 to 100 mg, more preferably 0.05 to 50 mg, and most preferably 0.1 to 20 mg of virosome for the symptomatic adjustment of dosage according to signs and symptoms of the patient in the course of treatment. The tablets may e.g. contain 0.001, 0.01, 0.05, 0.1, 0.5, 1, 2.5, 10, 20, 50, or 100 milligrams of virosome. An effective amount of virosome in the medicament prepared according to an embodiment the inventive use is ordinarily supplied at a dosage level of from about 0.0001 mg/kg to about 50 mg/kg of body weight per day. More particularly, the range is from about 0.0001 mg/kg to 7 mg/kg of body weight per day. If given to children, the dosage may be reduced appropriately.

Furthermore, the medicament prepared according to the inventive use can be administered in intranasal form, or via transdermal routes known to those of ordinary skill in the art. To be administered in the form of a transdermal delivery system, the administration dosage will, of course, be continuous rather than intermittent throughout the dosage regimen.

The medicament prepared according to the inventive use may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates, and cross-linked or amphipathic block copolymers of hydrogels.

A suitable formulation of the medicament prepared according to the inventive use for topical administration may be, for example, in the form of a solution, cream, ointment, gel, lotion, shampoo, or aerosol formulation adapted for application to the skin. These topical pharmaceutical compositions containing the medicament prepared according to the inventive use ordinarily include about 0.005% to 5% by weight of the active compound, i.e. the virosome, in admixture with a pharmaceutically acceptable vehicle.

Regardless of the route by which the medicament prepared according to the inventive use is administered, it is to be administered in an effective amount. An effective amount is that amount of a pharmaceutical preparation that, alone or together with further doses, stimulates the desired non-specific immunostimulatory response.

Moreover, when desired or necessary, suitable binders, lubricants, disintegrating agents and coloring agents can also be incorporated into the medicament as prepared by the inventive use. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methylcellulose, aga, bentonite, xanthan gum and the like.

The liquid forms of the medicament as prepared by the inventive use may be suitably flavored by suspending or dispersing agents such as the synthetic and natural gums, for example, tragacanth, acacia, methyl cellulose and the like. Other dispersing agents, which may be employed, are glycerin and the like. For parenteral administration, sterile suspensions and solutions are desired. Isotonic preparations, which generally contain suitable preservatives, are employed when intravenous administration is desired. Topical preparations containing the active drug component can be admixed with a variety of carrier materials well known in the art, such as, for example, alcohols, aloe vera gel, allatoin, glycerin, vitamins A or E oils, mineral oil, PPG2 myristoyl propionate, and the like, to form, for example, alcoholic solutions, topical cleansers, cleansing creams, skin gels, skin lotions, and shampoos in cream or gel formulations.

In one embodiment, the medicament as prepared by the inventive use may further comprise at least one adjuvant enhancing and/or, mediating an immune response, for example an innate immune response, a $Th_1$ or $Th_2$ response. Suitable adjuvants may enhance the immunological response by activating macrophages and/or stimulating specific sets of lymphocytes. A suitable adjuvant may be any ligand suitable for the activation of a pathogen recognition receptor (PRR). Immune response-potentiating compounds are classified as either adjuvants or cytokines. Adjuvants may enhance the immunological response by providing a reservoir of antigen (extracellularly or within macrophages), activating macrophages and stimulating specific sets of lymphocytes.

Adjuvants of many kinds are well known in the art; specific examples include Freund's (complete and incomplete), mycobacteria such as BCG, *M. vaccae*, or *Corynebacterium parvum*, Cholera toxin or tetanus toxin, *E. coli* heat-labile toxin, quil-saponin mixtures such as QS-21 (SmithKline Beecham), MF59 (Chiron) and various oil/water emulsions (e.g. IDEC-AF). Other adjuvants which may be used include, but are not limited to: mineral salts or mineral gels such as aluminium hydroxide, aluminium phosphate, and calcium phosphate; surface active substances such as lysolecithin, pluronic polyols, polyanions, peptides, keyhole limpet hemocyanins, and dinitrophenol, immunostimulatory molecules, such as saponins, muramyl dipeptides and tripeptide derivatives, short nucleic acid stretches such as CpG dinucleotides, CpG oligonucleotides, monophosphoryl Lipid A, and polyphosphazenes, particulate and microparticulate adjuvants, such as emulsions, liposomes, virosomes, cochleates, or immunostimulating complex adjuvants.

Cytokines are also useful due to their lymphocyte stimulatory properties. Many cytokines useful for such purposes will be known to one of ordinary skill in the art, including interleukin-2 (IL-2), IL-12, GM-CSF and many others. Furthermore ligands from the chemokine family, such as RANTES (Regulated upon Activation Normal T cell Expressed and Secreted), a lipoprotein of Gram-positive bacteria, a yeast cell wall component, a double-stranded RNA, a lipopolysaccharide of Gram-negative bacteria, flagellin, a U-rich single-stranded viral RNA, a Suppressor 6f Cytokine Signalling small interfering RNA (SOCS siRNA), a Pan DR epitope (PADRE) and mixtures thereof are suitable.

For treatment and prevention of cancers and/or metastases, the medicament as prepared by the inventive use may be administered in combination with a pharmaceutically acceptable carrier adopted for topical administration. Additionally, for the treatment and prevention of cancer, tumors and/or metastases, or viral infections, the medicament as prepared by the inventive use may be used together with other agents known to be useful in treating such malignancies. For combination treatment with more than one active agent, where the active agents can be administered concurrently, the active agents can be administered concurrently, or they can be administered separately at staggered times.

A further aspect of the invention relates to a non-specific stimulation of the immune system of an animal by means of administration of a virosome according to the present invention. It is desirable to increase the general resistance against diseases, especially against infectious and neoplastic diseases by means of a non-specific stimulation (a wake up call) of the body's immune system. Such a non-specific stimulus can be achieved by administration of virosomes. The administration, single or repeated, may take place before, during, or after exposure to infectious agents or the diagnosis of a disease, as a prophylactic, metaphylactic, therapeutic, or adjuvant treatment, respectively.

The specific embodiments of the invention and the following examples are provided to demonstrate the efficiency of the claimed invention but are not to be interpreted as limiting the scope of the invention. To the extent that specific materials are mentioned, it is merely for purposes of illustration and is not intended to limit the invention. Unless otherwise specified, biochemical and molecular biology procedures, such as those set forth in Voet, Biochemistry, Wiley, 1990; Stryer, Biochemistry, W. H. Freeman, 1995; Bodanszky, Peptide Chemistry. A Practical Textbook, 2nd ed., Springer-Verlag, Berlin, 1993; Sambrook et al., Molecular Cloning, Cold Spring Harbor Laboratory, 2001; Ausubel et al. (Eds.), Current Protocols in Molecular Biology, John Wiley & Sons, 2000 are used. One skilled in the art may develop equivalent means or reactants without the exercise of inventive capacity and without departing from the scope of the invention.

It will be understood that many variations can be made in the compositions and procedures herein described while still remaining within the bounds of the present invention. It is the intention of the inventors that such variations are included within the scope of the invention.

EXAMPLES

Content
1. Viruses
2. Propagation of viruses
3. Preparation of virosomes
3.1 Reagents
3.2 Preparation of standard virosomes (IRIV)
3.3 Preparation of standard virosomes with integrated heterologous antigen (IIRIV)
3.4 Preparation of standard virosomes containing TC-chol (TIRIV)
3.5 Preparation of TIRIVs containing heterologous antigen
3.6 Heterologous antigens used to formulate virosomes
4. Analytical assays
4.1 SDS-PAGE
4.2 Particle size determination: mean diameter/polydispersity (Table 1)
4.3 SRD (HA concentration)
4.4 Western Blot
4.5 FRET improved fusogenicity
5. Immunogenicity assays
5.1 Improved antigenicity
5.2 IFN γ staining improved immunogenicity
5.3 Comparison of HA derived from virus produced on egg and HA derived from virus produced in cell culture 1. Viruses The viruses used are influenza A/New Caledonia/20/99 (H1N1) and influenza A/Singapore/6/86 (H1N1).

2. Propagation of Viruses

Viruses were either propagated in the allantoic cavity of embryonated eggs (Gerhard, 1996), or on cell lines derived from avian embryonic stem cells (WO2006/108846). Viruses propagated in the allantoic cavity of embryonated eggs were obtained from Berna Biotech AG (Bern, Switzerland); viruses propagated on cell lines derived from avian embryonic stem cells were obtained from Vivalis (Roussay, France).

Egg-derived virus was purified and concentrated via sucrose gradient ultracentrifugation and inactivated by BPL. The virus produced on avian cell lines (EBx, either chicken (EB14) or duck) was represented by cell culture supernatant derived from cultures of influenza A infected EBx cells. This supernatant was concentrated and purified by ultracentrifugation prior to the analysis. The quantification of the virus proteins was done by single radial diffusion (SRD) (Wood et al, 1977).

The hemagglutinin/phospholipid ratio was determined according to Böttcher (Böttcher et al., 1961) and HA-quantification after SDS-PAGE with the Coomassie-extraction method as described by Ball, 1986.

3. Preparation of Virosomes 3.1 Reagents

Octaethyleneglycol-mono-(n-dodecyl)ether (OEG, $C_{12}E_8$), dimethylsulfoxide (DMSO), hydroxylamine hydrochloride, 1,2-Dipalmitoyl-sn-glycero-3-phospho-rac-(1-glycerol) (PG), acetonitrile, triethylammonium phosphate (TEAP) solution, sucrose, streptomycin, Hepes, penicillin and RPMI medium are purchased from Fluka Chemie GmbH and Sigma (Buchs, Switzerland), respectively. Sucrose (Eur. Phar.) is purchased from Merck (Dietikon, Switzerland). FCS was purchased from Gibco BRL (Basel, Switzerland). Egg phosphatidyl choline (PC) is obtained from Lipoid (Cham, Switzerland). 1-Oleoyl-3-palmitoyl-rac-glycero-2-phosphoethanolamine (PE) is obtained from Bachem (Bubendorf, Switzerland). Bio-Beads SM2 are purchased from Bio-Rad Laboratories (Glattbrugg, Switzerland). 1,2-Dipalmitoyl-sn-glycero-3-phosphoethanolamine-N-[4-(p-maleimidomethyl)cyclohexane-carboxamide] (N-MCC-PE) is purchased from Avanti Polar Lipids (Alabaster, USA). N-(4,4-difluoro-5,7-diphenyl-4-bora-3a,4a-diaza-s-indacene-3-propionyl)-1,2-dihexadecanoyl-sn-glycero-3-phosphoethanolamine (Bodipy 530/550-DHPE), Lissamine rhodamine B 1,2-dihexadecanoyl-sn-glycero-3-phosphoethanolamine triethylammonium salt (N—Rh-DHPE) and biotin-DHPE (N-(biotinoyl)-1,2-dihexadecanoyl-sn-glycero-3-phosphoethanolamine, triethylammonium salt) were from Molecular Probes Europe (Leiden, The Netherlands). Sephadex G-50 coarse was obtained from Amersham Biosciences (Otelfingen, Switzerland). IL-2 is obtained from EuroCetus B.V. (Amsterdam, The Netherlands). N-succinimidyl-S-acetylthioacetate (SATA) is purchased from Pierce Biotechnology (Rockford, USA). Cholesteryl N-(trimethylammonioethyl) carbamate chloride (TC-chol) was purchased from Merck Eprova (Schaffhausen, Switzerland).

3.2 Preparation of Standard Virosomes (Immunostimulating Reconstituted Influenza Virosomes, IRIVs)

For a final volume of 4 ml, 32 mg egg PC, 8 mg PE are dissolved in 3 ml of PBS containing 100 mM OEG (PBS/OEG). Inactivated influenza virus containing 2 mg HA is centrifuged at 100,000×g for 1 h at 4° C. and the pellet is dissolved in 1 ml of PBS/OEG. The detergent solubilised phospholipids and viruses are mixed in a final volume of 4 ml and sonicated for 1 min. This mixture is centrifuged at 100,000×g for 1 h at 18° C. Virosomes are then formed by detergent removal using two times 1.5 g of wet SM2 Bio-Beads (BioRad, Glattbrugg, Switzerland) for 1 h at room temperature with shaking. Virosomes are then sterile filtered (0.22 μm) and stored at 4° C.

3.3 Preparation of the Standard Virosomes with Integrated Heterologous antigens (IIRIVs)

For a final volume of 4 ml, 32 mg egg PC, 8 mg PE and the wanted amount of the heterologous antigen-PE conjugate are dissolved in 3 ml of PBS, 100 mM OEG (PBS/OEG). Inactivated influenza A/Singapore/6/86 virus containing 2 mg HA is centrifuged at 100,000×g for 1 h at 4° C. and the pellet is dissolved in 1 ml of PBS/OEG. The detergent solubilised phospholipids and viruses are mixed and sonicated for 1 min. This mixture is centrifuged at 100,000×g for 1 h at 18° C., Virosomes are then formed by detergent removal using two times 1.5 g of wet SM2 Bio-Beads (BioRad, Glattbrugg, Switzerland) for 1 h at room temperature with shaking. Virosomes are then sterile filtered (0.22 μm) and stored at 4° C.

3.4 Preparation of Virosomes Containing TC-Chol (TIRIVs)

TIRIVs are prepared by the detergent removal method. For a final volume of 4 ml, 32 mg egg PC, 8 mg PE, 5 mg cholesteryl N-(trimethylammonioethyl)carbamate chloride (TC-chol) and 200 mg of sucrose are dissolved in 3 ml of PBS, 100 mM OEG (PBS/OEG). 1-2 mg HA of inactivated influenza virus is centrifuged at 100,000×g for 1 h at 4° C. and the pellet is dissolved in 1 ml of PBS/OEG. The detergent solubilised phospholipids and viruses are mixed and sonicated for 1 min. This mixture is centrifuged at 100,000×g for 1 h at 18° C.

Virosomes are then formed by detergent removal at room temperature with shaking two times for 60 min each with 1.5 g of wet Bio-Beads SM2 each. The virosomes are sterile filtered (0.22 µm) and aliquoted in sterile glas vials. The closed vials are frozen at −70° C. and then lyophilized at −40° C. for 20 h and 10° C. for 2 h. The closed vials are stored at frozen until use.

3.5 Preparation of TIRIVs Containing Heterologous Antigen

To obtain TIRIVs containing heterologous antigen of choice, the antigen is dissolved in water at the desired concentration. Frozen, lyophilized TIRIVs are removed from the freezer and equilibrated at RT for 2-5 min, before an equal amount of dissolved heterologous antigen (4° C.) is added to the lyophlisate. The vial is mixed shortly for about 10 sec on the vortex on intermediate level and stored at 4° C. until use.

Alternatively, peptides which are linked to PE may be added to the TIRIVs during the preparation process described in example 5. The peptide is added at the desired concentration before sonication and sterile filtration of the mixture. The other preparation steps remain unchanged. Reconstitution of the lyophilized TIRIVs is done with an equal volume of water.

3.6 Heterologous Antigens used to Formulate Virosomes

The heterologous antigens used were malaria derived antigen UK 39 (WO2004/106366) from *Plasmodium falciparum* (UK 39); and HCV core 132: Hepatitis C virus derived antigen (HCV core 132).

4. Analytical Assays 4.1 SDS-Poly-Acrylamide-Gel-Elektrophoresis (SOS-PAGE)

Samples to be analyzed were mixed with the appropriate sample buffer supplied by Invitrogen (Basel, Switzerland) with or without reducing agent (Invitrogen) and incubated at 85° C. for 2 minutes. 5-10 µl of the sample were applied on polyacrylamide-gel-matrix (lnvitrogen, Basel, Switzerland) and run according to manufacture's instructions. Gels were either further analyzed by Western blot analysis and/or stained by silver staining using the SilverQuest Kit (Invitrogen, Basle, Switzerland) following the "fast staining"-protocol supplied by the manufacturer.

4.2 Particle Size Determination (Mean Diameter/Polydispersity)

In the table below, the concentration of hemagglutinin in mg/ml and the mean diameter of the virosomal particles is given. The polydispersity given in the last row is an indication for the homogeneity of the particle size in the solution. A particle solution with a polydispersity of below 0.3 is accepted for virosomes as vaccines, a value below 0.1 is considered to be very homogenous (homogeneity was determined by dynamic light scattering with a Zetasizer 1000HS instrument).

Size determination was performed by dynamic light scattering using a Zetasizer 1000HS instrument (Malvern Instruments) equipped with a standard 10 mW He—Ne laser ($\lambda$=633 nm) and an avalanche photodiode (APD). 5-20 µl of sample was added to filtered PBS buffer in a final cuvette volume of 1 ml. The measurements were performed at T=25° C. at the fixed scattering angle of 90°. The size distributions were evaluated by selecting the proper fitting.

4.3 SRD Analysis (Determination of HA Concentration)

The single-radial-immunodiffusion tests for determination of hemagglutinin in egg- and cell-based influenza batches described above were performed according to the procedure described by Wood et al. (Wood et al, 1977). Virions were disrupted by incubation in 1% Zwittergent (Calbiochem) for 30 min at room temperature (RT) and submitted to immunodiffusion for 72 h at RT in antibody-loaded agarose gels. The precipitation zone diameters of antigen—antibody complexes were measured and the antigen content of the virus preparations was calculated by using a calibration curve of a whole virus reference batch (NIBSC, London) with known HA content as communicated by the provider NIBSC. The whole virus reference batches used for HA quantification of cell-based influenza batches were their egg-based standardized counterparts from the NIBSC, as well as the antisera used.

TABLE 1

Determination of average size and polydispersity of IRIV in different formulations for the heterologous malaria-derived antigen UK 39. The size and the polydispersity were measured by dynamic light scattering using a Zetasizer 1000HS instrument (Malvern Instruments)

| | Sample Description | HA Concentration (mg/mL) | Z Average Mean (nm) | Poly-dispersity |
|---|---|---|---|---|
| 1. | UK39 IRIV_Chicken | 0.26 | 116 | 0.12 |
| 2. | UK39 IRIV_Duck | 0.25 | 117 | 0.14 |
| 3. | UK39_IRIV_Egg | 0.18 | 116 | 0.05 |

4.4 Western Blot

The comparative analysis of the influenza virus produced on embryonated eggs and avian cell lines included SDS-PAGE and Western blot analysis of the virus preparations to gain information about the synthesis and processing of virus hemagglutinine (HA) in both cell types: The SDS-PAGE was performed in order to analyze the purity and the protein content of the viral suspension and to identify the proteins/protein-sizes of HA and NA.

Samples to be analyzed were run on an SDS-PAGE as described above. Gels were transferred to appropriate transfer-buffer supplied by the manufacturer (Invitrogen, Basel, Switzerland). In parallel PVDF-membrane (Invitrogen, Basel, Switzerland) was pre-incubated in Methanol and transferred to transferbuffer as well. 4-5 blotting pads and 2 Watman-papers (Biorad, Reinach, Switzerland) per gel were soaked with transfer-buffer and the blot was assembled. The transfer was achieved by applying 25V, 125 mA, 17 W per gel for 1 h 30 min. Membranes were washed briefly in PBS containing 0.2% Tween 20 and unspecific binding of antibodies or sera was blocked by incubation with 5% milk in PBS for 2 h. After washing membranes again in PBS/0.2% Tween 20, blots were incubated with first antibody/serum diluted in 0.5% milk in PBS/0.2% Tween 20 1:100 up to 1:10'000 depending on the antibody at RT for 1-2 h. Membranes were washed 3 times for 5 minutes in PBS/0.2% Tween 20 and incubated in appropriate horseradish-peroxidase (HRP)-labelled secondary antibody diluted 1:1'000 up 1:20'000 in 0.5% milk in PBS/0.2% Tween 20. After washing the membranes for 5 times in PBS/0.2% Tween 20, visualization was done by chemiluminescence using SuperSignal West Dura kit (Pierce, Lausanne, Switzerland) according to manufacturer's instruction.

4.5 FRET Assay

For in vitro fusion measurements by fluorescence resonance energy transfer (FRET), the following assay was developed: 0.75 mol % of Bodipy 530/550-DHPE and 0.25 mol % of N—Rh-DHPE were incorporated into liposomes consisting of PC/PG (70:30). Fluorescence measurements were carried out in 5 mM sodium phosphate buffer pH 7.5, 100 mM NaCl, in a final volume of 0.8 ml in 2.5 ml PMMA microcuvettes (VWR, Dietikon, Switzerland) under continuous stirring. Typically, 1 µl of labelled liposomes (0.3 nmol phospholipid) were mixed with 5-20 µl of virosomes and fusion was triggered by addition of 3.75-7 µl of 1 M HCl, resulting in a pH of 4.5. The increase in fluorescence was recorded every 5 seconds at excitation and emission wavelengths of 538 nm and 558 nm, respectively, with an excitation slit of 2.5 nm and an emission slit of 15.0 nm. Measurements were carried out with an LS 55 Luminescence spectrometer (Perkin Elmer Instruments, Schwerzenbach, Switzerland) equipped with a thermostated cuvette holder and a magnetic stirring device. The instrument temperature setting was 42° C., resulting in sample temperature of 35° to 37° C. The maximal fluorescence at infinite probe dilution was reached after addition of Triton X-100 (0.5% v/v final concentration). For calibration of the fluorescence scale the initial residual fluorescence of the liposomes was set to zero and the fluorescence at infinite probe dilution to 100% (maximal fluorescence).

Samples for the FRET assay should contain a total amount of HA ranging from 0.5 to 10 µg HA. For analysis of virosomal formulations, 2 to 6 µg HA has proven optimal. The HA concentration of the sample is previously determined by SRD. Depending on the specific HA concentration of the formulation, the volume of virosomal formulation necessary for the FRET assay varies between 3 and 40 µl (corresponding to 2 to 6 µg HA). If the volume of the virosome sample is less than 40 µl, the difference is compensated for by addition of PBS.

It is emphasized that the ratio between HA and virosomal lipids remains unchanged if different amounts of virosomes are used in the FRET assay, e.g. in serial measurement as shown in Table 2.

Interpretation of FRET Results

Because the percentage values obtained in the FRET assay are variable, an absolute range/cutoff value is difficult to establish. In contrast, the ratio between different samples is relatively robust. The amount of HA used in the assay should be in the range of 3 to 6 µg in a total volume of 0.8 ml. Multiple measurements with different amounts within this range (e.g. 3, 4, 5, 6 µg) allow to plot a dose response curve that provides additional information (e.g. saturation of the system).

TABLE 2

Evaluation of the fusion activity of IRIV in different formulations for heterologous malaria derived antigen UK 39. For each formulation four aliquots with different HA amount were measured.

| | Sample Description | HA amount (µg) | Fusion activity (%) | |
|---|---|---|---|---|
| | | | Experiment 1 | Experiment 2 |
| 1. | UK39 IRIV_Chicken | 5.2 | 46 | 39 |
| | | 3.4 | 28 | 23 |
| | | 1.6 | 29 | 26 |
| | | 0.8 | 29 | 18 |
| 2. | UK 39 IRIV_Duck | 5.3 | 54 | 54 |
| | | 3.5 | 42 | 33 |
| | | 1.8 | 22 | 38 |
| | | 1.0 | 28 | 13 |
| 3. | UK 39 IRIV_Egg | 5.2 | 19 | 14 |
| | | 3.6 | 15 | 8 |
| | | 1.8 | 18 | 13 |
| | | 0.9 | 6 | 5 |

For each HA concentration analyzed by FRET, the results (expressed as % fusion activity) are compared between IRIVs comprising HA from chicken and egg-derived viruses. This is done by calculation of the ratio between the two samples for each HA concentration tested. Subsequently, the mean value of the ratios at different HA concentrations is calculated. The direct readout (% fusion acitivity) varies significantly between different HA concentrations (dose dependence), and also between different test runs (test variability) with the same sample. In contrast, the mean ratio shows much less variation and thus, represents a robust readout that allows a reproducible comparison between samples.

5 µg:39%:14%=2,78
3 µg:23:8=2,87
2 µg:26:13=2,0
1 µg:18:5=3.6

Figure 2:
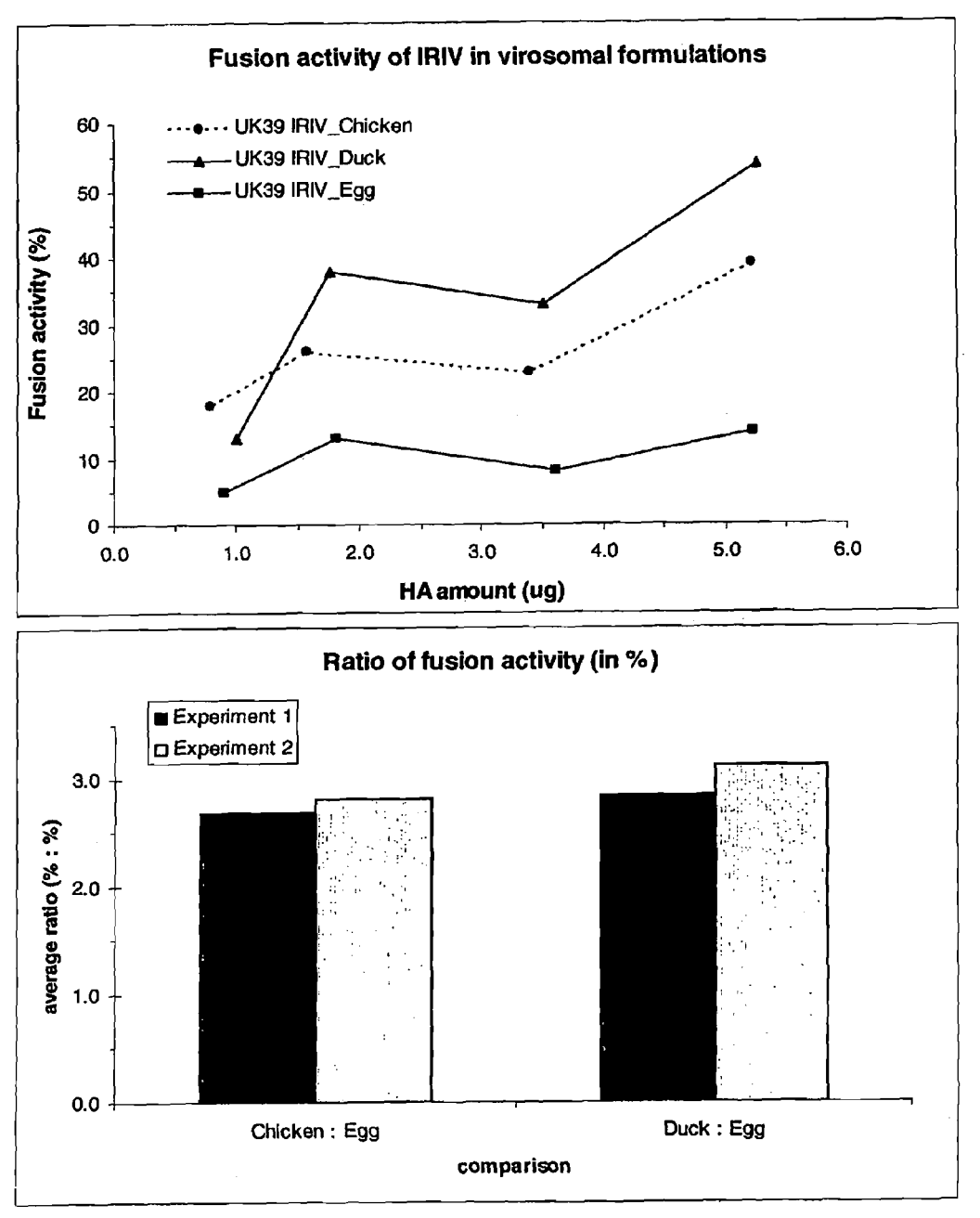

Resulting in a mean value of 2,81 (FIG. 2, lower panel)

5. Immunogenicity Studies

Immunogenicity Studies in Mice

Antibody response: If not indicated otherwise, groups of at least 10 BALB/c mice were immunized i.m. with 0.1 ml empty IRIVs or IRIVs loaded with heterologous antigens (IIRIVs) in different concentrations to evaluate the immune response. In this experiment, the malaria antigen UK39 served as the heterologous antigen. Two vaccinations at an interval of three weeks were applied, and serum samples were collected two weeks after the second immunization.

CD8+ T cell response: If not indicated otherwise HLA-A2 transgenic mice were immunized s.c. with 0.1 ml empty TIRIVs or TIRIVs loaded with heterologous antigens to evaluate the immune response. Two vaccinations at an interval of three weeks were applied, and spleen cells were collected two weeks after the second immunization.

5.1 Immunological Analysis by ELISA (B-Cell Response)

Figure 4:
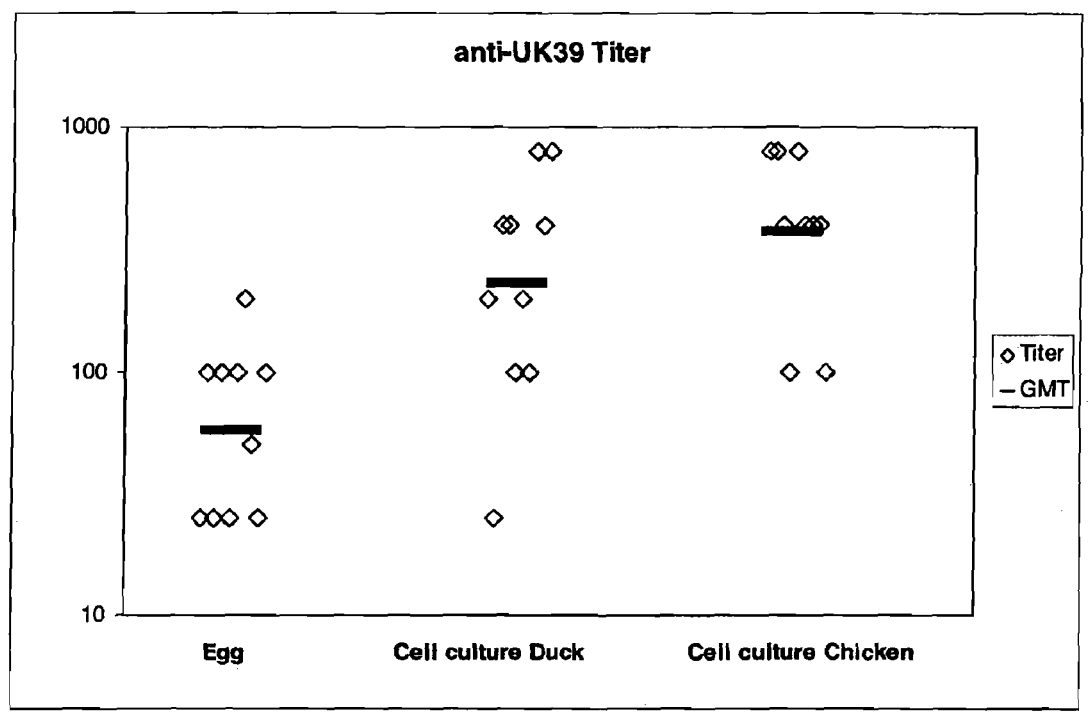
Figure 5:
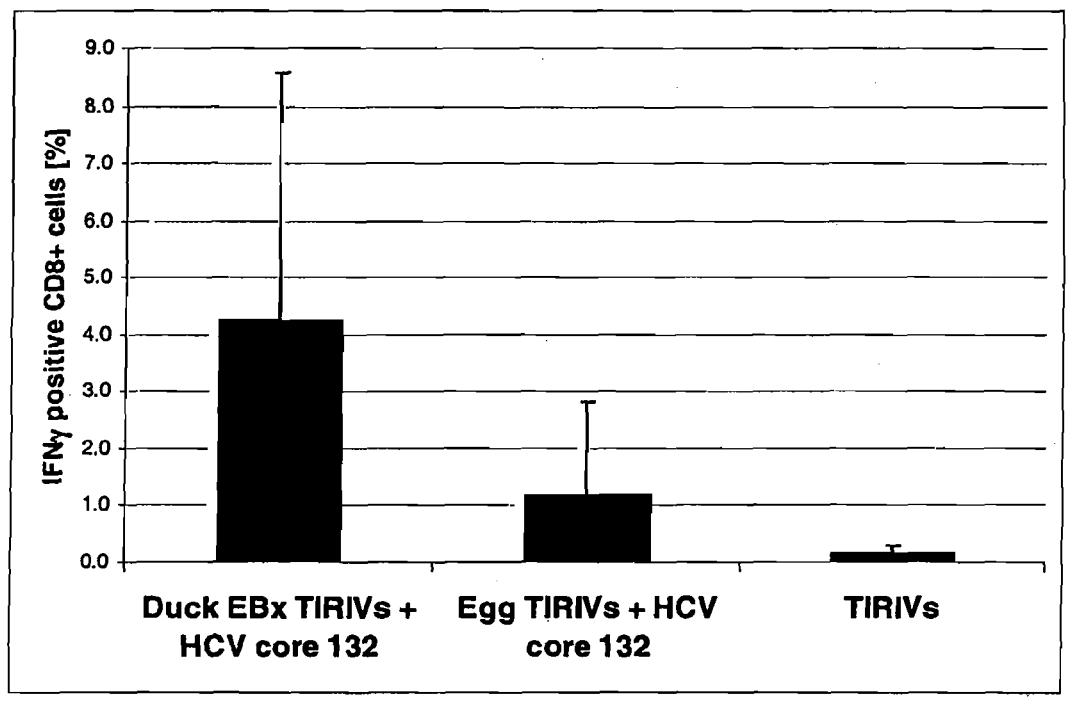
FIG. 5 shows the improved induction of CD8+T cells specific for a heterologous (non HA) antigen by virosomes comprising HA prepared from viruses derived from (avian) cell lines and loaded with heterologous antigen, compared to virosomes comprising HA prepared from viruses derived from egg.

Groups of at least 10 BALB/c mice are immunized twice i.m. at an interval of three weeks and serum samples are collected. Schedule, dosage and number of immunizations may vary as long as the same procedure is applied to the groups compared. The sera are tested by ELISA to measure the antibody responses against influenza HA (FIG. 3) and against the heterologous antigen UK39 derived from *Plasmodium falciparum* (FIG. 4). For each serum, the antibody titer against the specified antigen is determined. This is done by calculating the dilution corresponding to the OD value 20% of the maximum OD-value of the control-serum included on each plate.

All individual titers per group are recorded. The groups are compared by applying the Wilcoxon test to the data (serum titer). A resulting p value smaller than 0.05 indicates a 95% probability that the two groups are not equal. Here, the Wilcoxon test is used to show that the improved virosomes are "significantly more immunogenic", i.e. a Wilcoxon test on serum titers yields a p value <0.05 when egg-derived and viroplus virosomes are compared.

Enzyme-linked immunosorbent assay (ELISA) analyses were performed in order to detect antibodies against heterologous antigens or HA in serum samples. Briefly, 96-well microtiter plates (Nunc, Fisher Scientific, Wohlen, Switzerland) were coated overnight at 4° C. with 100 µl per well of the antigen of interest in the adequate buffer system., e.g. malaria-antigen UK 39 phosphatidylethanolamine conjugates were coated as 10 µg/ml solution in PBS (pH 7.4) onto Polysorb microtiter plates, while HA proteins (inactivated whole virus or virosomal formulation) were coated as 1 µg/ml solution in 0.05M carbonate buffer pH 9.4 onto Maxisorb microtiter plates.

After coating, the plates were blocked with 5% milk powder in PBS for 2 h minimum at RT, followed by three washes with PBS containing 0.05% Tween 20. Plates were then incubated with serial dilutions (starting at 1:50) of the mouse serum in PBS containing 0.05% Tween 20 and 0.5% milk powder for 2 h at 37° C. Each plate must contain a positive control serum. After a further washing cycle, the plates were incubated with HRP-conjugated goat anti-mouse Ig antibody (BD Bioscience, Basel, Switzerland) for 1 h at 37° C. After a last washing cycle, OPD-substrate (O-Phenylendiamine tablets, Fluka, Buchs, Switzerland, 1 tablet in 50 ml citrate buffer+20 µl $H_2O_2$) was added, and the plates were incubated in the dark at room temperature until the colorimetric reaction had progressed sufficiently and reaction was stopped by addition of 100 µl M $H_2SO_4$ and optical densities (OD) were read at 492 nm on a Spectra Max Plus (Molecular Devices, Bucher Biotech, Basel, Switzerland).

As shown in FIG. 4, the differences in the immunogenicity observed between IIRIVs (IRIVs loaded with UK39) comprising HA derived from virus produced on eggs and IIRIVs comprising HA derived from virus produced in cell lines are significant: p=0.002 for chicken cell culture vs. egg and p=0.009 for duck cell culture vs. egg. There is an improved immunogenicity of UK39 associated with virosomes formulated with HA from EBx-derived virus compared to UK39 associated with virosomes formulated with HA from egg-derived virus. The gray dashed line marks the OD-value to calculate the anti UK39-titer calculated as 20% of the maximum OD 492 value of the control included on each plate.

5.2 Immunological Analysis by Intracellular IFN-γ Staining (T-Cell Response)

Intracellular IFNγ staining: Spleen cells ($12 \times 10^6$) were incubated with 10 µg/ml specific peptide or non-relevant peptide (negative control) in complete RPMI medium containing 2 mM L-Glutamine, 100 U/ml Penicillin, 100 µg/ml Streptomycin, 5 mM Hepes, 5% FCS and $5 \times 10^{-6}$ M 2-mercaptoethanol at 37° C. and 5% CO2 in the presence of 5 µg/ml Brefeldin A for 4 h. Cells were stained with FITC-conjugated anti-CD8 antibodies, permeabilized, and stained with PE-conjugated anti-IFNγ antibodies using the Cytofix/Cytoperm kit following the manufacturer's instructions (BD Pharmingen, San Diego, USA). Data were acquired on a BD™ LSR II flow-cytometer and analyzed with FlowJo software. Frequency of IFNγ-producing cells was calculated as percentage of IFNγ positive and CD8 positive cells among total CD8 positive cells. The percentage of peptide-specific cells was obtained by subtracting the percentage in samples stimulated with non-relevant peptide from the percentage in samples stimulated with specific peptide.

HLA-A2 transgenic mice were immunized twice s.c. at an interval of three weeks with TIRIVs prepared with cell culture derived influenza virus (Duck EBx TIRIVs) or TIRIVs prepared with egg derived virus (egg TIRIVs), both loaded with the heterologous antigen HCV. core 132. For both preparations the amount of HA was identical. Control mice were immunized with TIRIVs without the heterologous antigen. Two weeks after the last immunization the frequency of CD8+ T cells specific for the heterologous antigen was determined by intracellular IFN-γ staining. Shown are mean values±standard deviation.

5.3 Comparison of HA Derived from Virus Produced on Egg and Virus Produced in Cell Culture As shown in FIG. 1, the polyclonal and monoclonal antibodies react differently with the egg-derived and with the avian cell culture-derived material. While the polyclonal serum reacts with both HA derived from virus produced in avian cell lines and with HA derived from virus produced on eggs, the monoclonal antibody only reacts with HA from egg-derived virus.

Deglucosylation of HA

Different strains of Influenza A (A/Singapore (H1/N1), A/NC (H1/N1), A/Panama (H3/N2) were amplified on embryonated egg; the HA derived from the respective preparations is recognized by the mAb, indicating that the mAb is not strain-specific. For deglycosylation, the "Enzymatic protein deglycosylation Kit" from Sigma-Aldrich (Buchs, Switzerland) was used. Preparations were done according to the manufacturer's instructions. Deglycosylation of the virus preparations from the three strains led in all cases to the complete loss of the signal, while a polyclonal serum directed against HA recognized bands of smaller size representing the deglycosylized protein (Table 3).

Passage of Influenza Virus on Mammalian Cell Line and Analysis by Western Blot

Two 6-well-plates with either MDCK- or Vero cells were prepared: $5 \times 10^5$ cells per well were seeded in Episerf medium. The following day cell were infected with virus grown on embryonated eggs or in EBx cells, either with or without Trypsin to generate infectious virions (by the cleavage of HA which renders the protein active) or to limit replication to one passage (by keeping HA in an inactive $HA_0$ conformation in the absence of trypsin), respectively. Cells were harvested by scraping off the cells after 1 day (for MDCK) or 3 days (Vero cells), as soon as the virus infection led to lysis of the cells or induced a visible CPE, respectively. The infected cells were subsequently analysed by Western blot analysis using either the polyclonal anti-HA-rabbit serum or the HA-specific mAb.

However, staining with the monoclonal antibody was only positive for the virus isolated from the infected egg (control) but negative for the HA-samples which were derived from virus passaged only once on mammalian cells (MDCK or Vero cells, as obtained in the absence of trypsin, which generates only viruses incapable to re-infect cells). Thus, one passage was sufficient to eliminate the signal with the mAb.

One passage excludes the possibility of amino acid exchange, and therefore, a modification of the epitope on amino acid level as reason for the loss of binding can be excluded. In the absence of trypsin, HA0 is not cleaved into HA1 and HA2. A destruction of the epitope by cleavage of HA by trypsin can be excluded as reason for the lack of antibody binding as well.

TABLE 3 comparison of hemagglutinin derived from influenza virus propagated on egg or on cell lines

| Influenza virus propagated on | Polyclonal Ab | Monoclonal Ab | after deglycosylation: Polyclonal Ab | after deglycosylation: Monoclonal Ab |
|---|---|---|---|---|
| Chicken cells | + | − | n.d. | n.d. |
| Duck | + | − | n.d. | n.d. |
| Egg | + | + | +, smaller sized bands | − |

TABLE 3-continued comparison of hemagglutinin derived from influenza virus propagated on egg or on cell lines

| Influenza virus propagated on | Polyclonal Ab | Monoclonal Ab | after deglycosylation: Polyclonal Ab | after deglycosylation: Monoclonal Ab |
|---|---|---|---|---|
| MDCK | + | − | n.d. | n.d. |
| Vero | n.d. (limited growth) | n.d. | n.d. | n.d. |
| 1. egg, 2. mammalian | + | − | n.d. | n.d. |

The invention claimed is:

1. A virosome comprising hemagglutinin (HA), wherein the HA is derived from influenza virus produced in an avian cell line, and wherein the fusion activity of said virosome is at least 50% higher compared to the average fusion activity of a virosome comprising HA that is derived from influenza virus produced in chicken eggs.

2. The virosome according to claim 1, wherein the immunogenicity of said virosome is significantly higher compared to the immunogenicity of a virosome comprising HA that is derived from influenza virus produced in chicken eggs.

3. The virosome according to claim 1, wherein the HA is derived from at least two different influenza virus strains.

4. The virosome according to claim 1, wherein the virosome is lyophilized.

5. The virosome according to claim 1, wherein the virosome is loaded with antigen.

6. The virosome according to claim 1, wherein the virosome is empty.

7. A pharmaceutical composition comprising a virosome according to claim 1.

8. The pharmaceutical composition according to claim 7, wherein the composition is a vaccine.

9. The pharmaceutical composition according to claim 7, wherein the compositions is immunogenic and further comprises a liposome and at least one antigenic molecule.

10. The pharmaceutical composition according to claim 9, wherein the at least one antigenic molecule is entrapped in said liposome.

11. A kit comprising a virosome according to claim 1.

12. A method of vaccinating or immunizing a subject with the virosome according to claim 5, said method comprising administering said virosome to said subject.

13. A method of delivering a virosome according to claim 1 to a subject afflicted with a disease or disorder, said method comprising administering said virosome to said subject, wherein said disease or disorder is infectious or neoplastic.

14. A method of preparing a virosome according to claim 1, comprising the steps of:
  a. treating a whole influenza virus with a detergent or short chain phospholipid, wherein said influenza virus is produced in an avian cell line;
  b. separating the HA containing fraction, optionally adding phospholipids;
  c. removing the detergent, resulting in the formation of the virosome.

15. A virosome obtainable by the method comprising the steps of
  a. treating a whole influenza virus with a detergent or short chain phospholipid,
  b. separating the HA containing fraction, optionally adding phospholipids,
  c. removing the detergent, resulting in the formation of said virosome;
    wherein said influenza virus is produced in an avian cell line,
    wherein the fusion activit of said virosome is at least 50% higher compared to the average fusion activity of a virosome comprising HA that is derived from influenza virus produced in chicken eggs.

16. A method of generating an immune response against an antigen, said method comprising administering a pharmaceutical composition comprising the virosome according to claim 1 and an antigen.

17. A method of non-specifically stimulating an immune response, said method comprising administering a pharmaceutical composition comprising the virosome of claim 6 as a non-specific immunostimulating agent.

18. A method of delivering a composition according to claim 7 to a subject afflicted with a disease or disorder, said method comprising administering said composition to said subject, wherein said disease or disorder is infectious or neoplastic.

* * * * *